United States Patent [19]

Millane

[11] Plant 5,148

[45] Nov. 29, 1983

[54] RED MAPLE TREE NAMED VASE

[76] Inventor: Cornelius A. Millane, 604 Main St., Cromwell, Conn. 06416

[21] Appl. No.: 412,022

[22] Filed: Aug. 26, 1982

[51] Int. Cl.[3] ..... A01H 5/12
[52] U.S. Cl. ..... Plt./51
[58] Field of Search ..... Plt./51

*Primary Examiner*—Robert E. Bagwill

*Attorney, Agent, or Firm*—Wm. A. Snow

[57] ABSTRACT

This disclosure concerns a new and distinct variety of Acer Rubrum, commonly known as red maple tree, characterized by its strong structure which resists storm damage extremely better than other red maples, the tendency of the tertiary branches to be short and spur-like, and the branching on young trees having a simple, bold appearance.

4 Drawing Figures

BACKGROUND OF THE INVENTION

This new variety red maple tree was discovered by me growing in a planting of red maple beds at Millane Nurseries in Cromwell, Conn., and grew to a height of thirty-eight feet in the shape of an upright vase, with a robust growth rate of twenty to thirty inches a year. I now have thousand trees growing at McGill's Nursery at Boring, Oreg. reproduced by budding.

SUMMARY OF THE INVENTION

A new and distinct cultivar of red maple tree characterized by its robust growth rate, the tendency of the tertiary branches to be short and spur-like, the leaf colors being variable in the Fall from day to day from vivid yellow orange 15C to red 53B to dark red 59B, the secondary branches being short and spur-like, the bark exfoliates, and this variety has a stronger trunk and branches compared to other maple trees.

BRIEF DESCRIPTION OF DRAWINGS

The color designations in this specification are according to the R.H.S. Colour Chart of The Royal Horticultural Society.

The upper photograph on the first sheet of photographs shows the tree of this new variety in the summer months.

The lower photograph shows the tree in the winter months.

The upper photograph of the second sheet of photographs shows the leaves in the summer. The photo shows the branch and leaves extending diagonally downwardly but actually the branch and leaves extend upwardly diagonally as shown in the lower photograph.

The bottom photo shows a stand of trees.

DETAILED DESCRIPTION OF THE NEW PLANT VARIETY

The following is a detailed description of my new variety of red maple tree, the stated observations having been made of trees growing in the Millane Nurseries at Cromwell, Conn. and were made by applicant and Richard A. Jaynes, Horticulturist of the Connecticut Agricultural Experimental Station in New Haven, Conn. The colors stated are taken from The Royal Horticultural Society Colour Chart.

Origin: Seedling.

Classification:
- *Botanic.*—Acer Rubrum.
- *Commercial.*—Red Maple.

Form: Tree.

Shape: Upright vase shape; Narrow at base and fuller at top.

Height: 38 feet.

Trunk size: 38" D.B.H. and very strong.

Growth rate: 20 to 30 inches per year.

Bark: Rough and exfoliates like a silver maple tree.

Strength: Strong.

Branches:
- *Angle of attachment.*—Ascending at about 30°.
- *Secondary branches.*—Tend to be short and spur-like.
- *Lateral growth.*—Resembles the spur type growth on apple trees. The buds on these spur-like growths are multiple with 2 or 3 times the amount of buds and leaves in one cluster. The lateral branch growth is stunted and appears spur-like.

Leaves:
- *Length.*—3½ to 5 inches.
- *Width.*—3½ to 5 inches.
- *Form.*—Three-lobed and 50% thicker and 50% larger than normal Acer Rubrum Red Sunset.
- *Margins.*—Crenate-serrate, deep sinuses between lobes.
- *Pubescense distribution.*—Along veins, especially at base of leaf; more abundant on young leaves.
- *Quantity.*—They tend to cluster and sheath primary branches.
- *Color.*—Summer — Green group, 146B on top of leaf green 137B and green 136B.
- *Petioles.*—Length: 1¼ to 4 inches with shorter ones near terminal.
- *Leaf blade base.*—Subcordate.
- *Color.*—Fall — 15C to 53B and 59A.

This variety clearly distinguishes from other red maple trees by its robust growth in a stand growing under similar field conditions, its strong structure which resists storm damage having survived, without breakage, in the ice storms in 1973, 1974, the tertiary branches tending to be short and spur-like, on young trees especially, the branching being simple and bold in appearance. The overall branch structure resembles an American Elm as compared with the rounded and oval form of other red maple trees. It grows terminally on all branches 18 to 34 inches a year plus, compared with other maples which grow approximately 12 to 15 inches a year in the area of Cromwell, Conn. The lateral growth on the branches resembles the spur-type of growth on apple trees. The buds on these spur-like growths are multiple with two to three times the amount of buds and leaves in one cluster. These observations were made by applicant and McGill's Nursery.

I claim:

1. A new and distinct variety of red maple tree as herein shown and described.

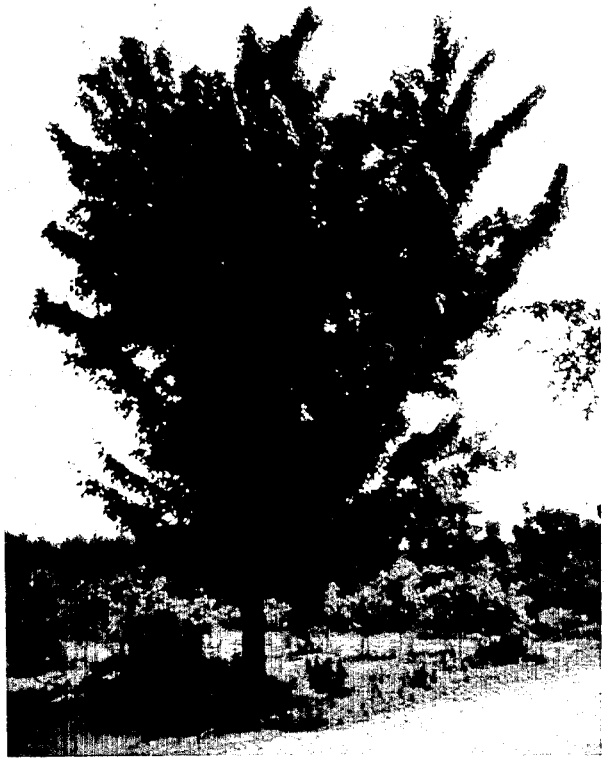
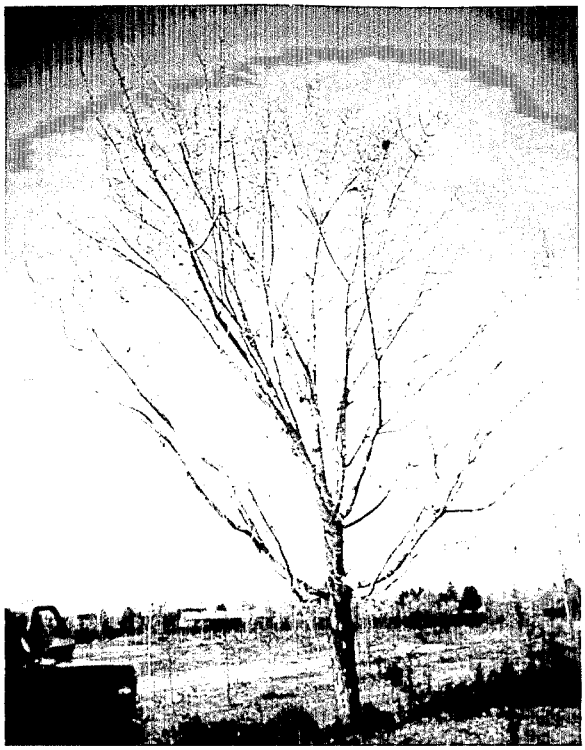

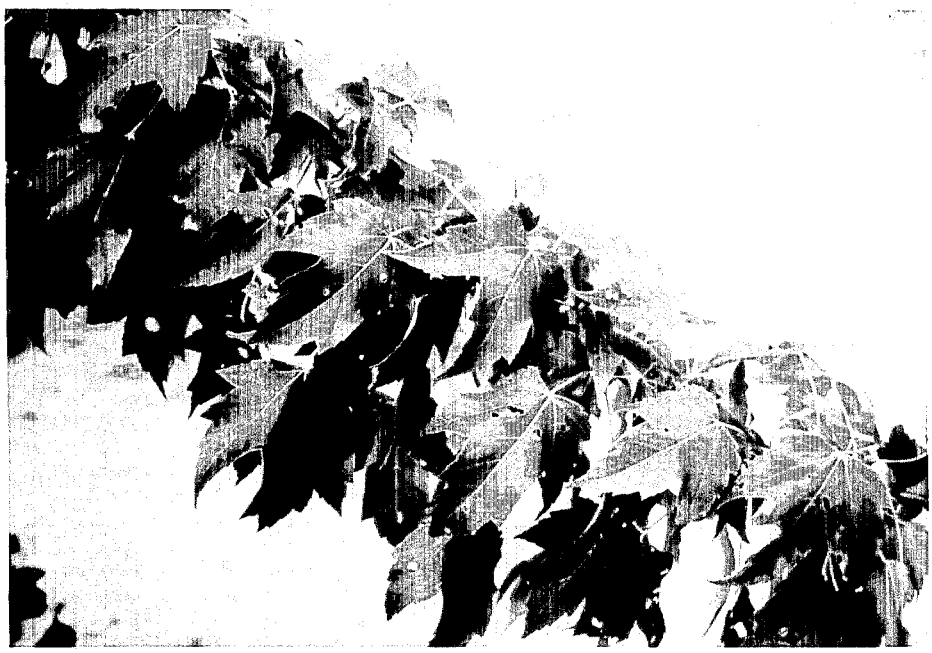
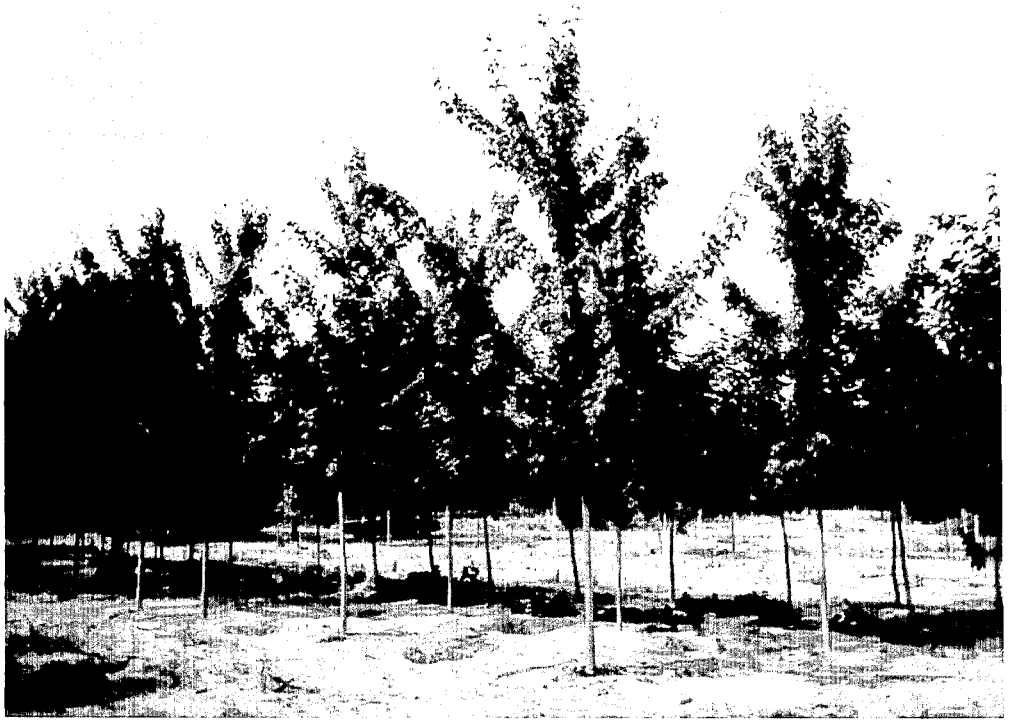

* * * * *